United States Patent [19]

Yoshida et al.

[11] Patent Number: 4,567,308

[45] Date of Patent: Jan. 28, 1986

[54] PROCESS FOR PREPARING ALKYLCYCLOPENTADIENE DERIVATIVES

[75] Inventors: Zenichi Yoshida, 281, Ginza-cho 4-chome, Fushimi-ku, Kyoto-shi, Kyoto-fu; Susumu Kato; Yasuhiro Amemiya, both of Osaka; Keisuke Yanai, Nara, all of Japan

[73] Assignees: Asahi Chemical Co., Ltd.; Zenichi Yoshida, both of Japan

[21] Appl. No.: 714,261

[22] Filed: Mar. 21, 1985

[30] Foreign Application Priority Data

Mar. 26, 1984 [JP] Japan ................................... 59-59070
Nov. 9, 1984 [JP] Japan ................................. 59-237272
Feb. 18, 1985 [JP] Japan .................................. 60-29927

[51] Int. Cl.$^4$ .............................................. C07C 2/02
[52] U.S. Cl. .................................. 585/375; 585/376; 502/340; 502/341; 502/344
[58] Field of Search ................ 585/375, 376; 502/340, 502/341, 344, 208, 306, 317, 328, 330

[56] References Cited

U.S. PATENT DOCUMENTS 3,255,267  6/1966  Fritz et al. ........................... 585/375
3,560,583  2/1971  Stewart et al. ....................... 585/375

FOREIGN PATENT DOCUMENTS 657800  2/1963  Canada ................................ 585/375

OTHER PUBLICATIONS

J. Org. Chem., 43, (21), 4090–4094 (1978).

*Primary Examiner*—John Doll
*Assistant Examiner*—A. Pal
*Attorney, Agent, or Firm*—Larson and Taylor

[57] ABSTRACT

An alkylation method of a cyclopentadiene derivative comprising the vapor-phase reaction of a cyclopentadiene derivative and an aliphatic lower alcohol in the presence of a specific heterogeneous basic catalyst.

8 Claims, No Drawings

PROCESS FOR PREPARING ALKYLCYCLOPENTADIENE DERIVATIVES

The invention relates to a process for preparing alkylcyclopentadiene derivatives.

Cyclopentadienes and alkylated products thereof are important as an additive for synthetic rubbers, starting materials for resins or industrial chemicals. One of the conventional processes for preparing alkylcyclopentadienes employs an organometallic compound. However, this process involves many reaction steps, danger of handling organometals, polymerization reaction as a side reaction. It is impossible to use this process industrially.

As an another prior art, Journal of the Chemical Society of Japan, 1977, page 375 discloses a process for preparing alkylcyclopentadienes by reacting a cyclopentadiene with ethylene in vapor-phase with use of silicone carbide. It is known two kinds of monoethylcyclopentadienes are produced by this method. However, by this method cannot be synthesized dialkylated, trialkylated, tetraalkylated and like polyalkylated cyclopentadienes, or methylated cyclopentadienes.

On the other hand, it is well known that aromatic compound such as benzene, toluene, xylene or phenol can be alkylated by an alcohol (especially methanol) in vapor-phase with use of zeolite catalyst as an acid catalyst. This method can produce a corresponding alkylated aromatic compound by an alkylation of benzene ring. This catalyst, however, when applied to the process for preparing alkylcyclopentadienes, cannot produce any alkylated derivative but forms a polymerized product, carbonized product on the catalyst and like products by side reactions.

The following alkylation processes are known in which cyclopentadiene derivative is alkylated with an alcohol.

Firstly, U.S. Pat. No. 3,255,267 discloses a preparation of alkylated derivatives of cyclopentadiene by a reaction of cyclopentadiene or an alkylcyclopentadiene with an alcohol in the presence of a strong basic catalyst such as potassium or sodium hydroxide or alkoxide. However, the reaction is carried out in a liquid-phase, for example, batchwise at an increased pressure with use of an autoclave, or continuously at a pressure of 4,000 psi. Further, attention should be drawn to the fact that, as disclosed in the patent, only a tarry product was obtained when alkylation of cyclopentadiene with methanol was attempted. Thus, the patent describes it is impossible to produce a methylated derivative of cyclopentadiene.

Hirsch and Bailey disclose a preparation of 1,2,3,4,5-pentabenzylcyclopentadiene by a reaction of cyclopentadiene dimer with benzyl alcohol and sodium benzyloxide under reflux condition (J. Org. Chem., Vol. 43, No. 21, 4090–4094, 1978). The reaction is also conducted in a liquid-phase and involves a removal of aqueous layer during reaction. Moreover, a gel of sodium benzoate deposits when the reaction mixture is allowed to cool. Thus, this process requires a cumbersome means to remove aqueous layer during reaction and has a problem in purification of a product and in recovery of the catalyst.

Further, none of alkylation is reported which comprises a reaction of cyclopentadienes with an aliphatic lower alcohol in vapor-phase.

An object of the invention is to provide a process for preparing alkylcyclopentadienes which comprises a reaction of cyclopentadienes with an aliphatic lower alcohol in vapor-phase with use of a specific catalyst.

The above and other objects of the invention will become apparent from the following description.

The present invention provides an alkylation method of a cyclopentadiene derivative comprising the vapor-phase reaction of a cyclopentadiene derivative and an aliphatic lower alcohol in the presence of the following heterogeneous basic catalyst (A), (B) or (C).

(A) ① at least one selected from the group consisting of oxides, hydroxides or salts of alkaline earth metals, and alkali metal salts;

(B) a mixture of the above ① and at least one selected from the group consisting of oxides and hydroxides of alkali metals;

(C) a mixture of at least one selected from the group consisting of oxides, hydroxides and salts of alkaline earth metals or alkali metals, and at least one selected from the group consisting of elements of groups (I) to (VIII), 2 to 7 periods of the periodic table and oxides, hydroxides and carbonates of these elements (provided that oxides, hydroxides and carbonates of alkaline earth metals and alkali metals are excluded).

Examples of useful cyclopentadienes in the invention are cyclopentadiene, cyclopentadiene dimer, monomethylcyclopentadiene, monomethylcyclopentadiene dimer and alkylated derivatives thereof.

Examples of aliphatic lower alcohols used in the invention are those having 1 to 4 carbon atoms. More concrete examples are methanol, ethanol, propanol and butanol.

It is characterized that catalysts adopted in this invention have a wide range of basicity expressed in H— or pKa.

The catalysts used in the invention are the following basic compound (A), (B) or (C).

(A) ① at least one selected from the group consisting of oxides, hydroxides or salts of alkaline earth metals, and alkali metal salts;

(B) a mixture of the above ① and at least one selected from the group consisting of oxides and hydroxides of alkali metals;

(C) a mixture of at least one selected from the group consisting of oxides, hydroxides and salts of alkaline earth metals or alkali metals, and at least one selected from the group consisting of elements of groups (I) to (VIII), 2 to 7 periods of the periodic table and oxides, hydroxides and carbonates of these elements (provided that oxides, hydroxides and carbonates of alkaline earth metals and alkali metals are excluded).

The "mixture" mentioned above includes not only a physical mixture but mixed compounds in which a part or all of compounds are chemically bonded. The term "mixture" is used hereinafter in the same meaning as above.

In the above, oxides and hydroxides of alkaline earth metals include BeO, MgO, CaO, SrO, BaO, $Mg(OH)_2$, $Be(OH)_2$, $Ca(OH)_2$, $Sr(OH)_2$, $Ba(OH)_2$, etc.

Examples of useful oxides and hydroxide of alkali metals are $Li_2O$, $Na_2O$, $K_2O$, $Rb_2O$, $Cs_2O$, NaOH, KOH, LiOH, RbOH, CsOH, etc.

Examples of salts of alkaline earth metals and alkali metals are carbonates, phosphates, aluminates, tungstates, molybdates, stannates, metavanadates, etc. of these metals. Salts of alkaline earth metals include basic magnesium carbonate, $CaCO_3$, $BaCO_3$, $SrCO_3$, MgWO$_4$, CaWO$_4$, BaWO$_4$, CaMoO$_4$, BaMoO$_4$, etc. Salts of alkali metals include Li$_2$CO$_3$, Na$_2$CO$_3$, K$_2$CO$_3$, Rb$_2$CO$_3$, Cs$_2$CO$_3$, Na$_3$PO$_4$, NaAlO$_2$, Na$_2$WO$_4$, K$_2$WO$_4$, Na$_2$MoO$_4$, Na$_2$SnO$_3$, NaVO$_3$, etc.

Examples of elements of groups (I) to (VIII), 2 to 7 periods of the periodic table or oxides, hydroxides or carbonates of these elements are C, Na, Ca, Mg, Sc, Ti, Mn, Fe, Co, Ni, Cu, Zn, Ga, Ge, Se, Y, Zr, Nb, Mo, Ru, Rh, Pd, Ag, Cd, In, Sn, Sb, Te, Hf, W, Re, Os, Ir, Pb, Bi, B$_2$O$_3$, Al$_2$O$_3$, SiO$_2$, P$_2$O$_5$, Sc$_2$O$_3$, TiO$_2$, V$_2$O$_3$, V$_2$O$_5$, CrO$_3$, Cr$_2$O$_3$, MnO$_2$, FeO, Fe$_2$O$_3$, Fe$_3$O$_4$, NiO, Ni$_2$O$_3$, CuO, Cu$_2$O, ZnO, Ga$_2$O$_3$, GeO$_2$, SeO$_2$, As$_2$O$_5$, Y$_2$O$_3$, ZrO$_2$, Nb$_2$O$_5$, MoO$_2$, MoO$_3$, RuO$_2$, PdO, Ag$_2$O, CdO, In$_2$O$_3$, SnO, SnO$_2$, Sb$_2$O$_3$, TeO$_2$, La$_2$O$_3$, CeO$_2$, Pr$_2$O$_3$, Nd$_2$O$_3$, Sm$_2$O$_3$, Eu$_2$O$_3$, Gd$_2$O$_3$, Tb$_4$O$_7$, Dy$_2$O$_3$, Ho$_2$O$_3$, Er$_2$O$_3$, Tm$_2$O$_3$, Yb$_2$O$_3$, HfO$_2$, Ta$_2$O$_5$, WO$_3$, OsO$_4$, Ir$_2$O$_3$, PtO$_2$.H$_2$O, Tl$_2$O$_3$, Ti(OH)$_4$, Cr(OH)$_3$, FeO(OH), Co(OH)$_2$, Ni(OH)$_2$, Zn(OH)$_2$, Zr(OH)$_4$, Cd(OH)$_2$, Ce(OH)$_3$, Bi(OH)$_3$, Th(OH)$_4$, MnCO$_3$, CdCO$_3$, La$_2$(CO$_3$)$_3$, Ce$_2$(CO$_3$)$_3$.5H$_2$O, basic cobalt carbonate, basic nickel carbonate, basic copper carbonate, basic zinc carbonate, etc. However, excluded are those which are gaseous at a room temperature but are included those having crystal water.

According to the invention, oxides, hydroxides or salts of the above metals are used in the commercial form, or used after calcined or after degassed at a reduced pressure.

Furthermore, usable are an element, hydroxide, carbonate, basic carbonate or organic acid salt of the above metals, ammonium salt of oxygen-containing acid of the above metals and metal salt or organometallic compound including the above metals which are treated at a high temperature. In addition, usable are those compounds which are produced by calcination of the precipitated hydroxides or hydrated amorphous metal oxide obtained by hydrolysing or neutralizing with an aqueous ammonia solution a metal salt, metal halide or the like.

The above metal element, organic acid salt thereof and the like can be converted to metal oxides or the like beforehand or in the course of the present vapor-phase alkylation.

Further, these catalysts (A) to (C) can be used as supported on the carrier according to the known method. The above catalyst preferably contains no impurity but may contain a small amount thereof.

These catalysts (A) to (C) are preferably calcined to enhance their activity at a temperature of 200° to 1000° C., more preferably at 400° to 800° C. in an atmosphere of air, nitrogen, helium, argon or like inert gas under normal, increased or reduced pressure.

Carbonized substances may adhere to the catalyst after a prolonged use thereof. In this case, it is possible to regenerate the catalyst by calcination at a temperature of 300° to 900° C., preferably at 400° to 800° C. in an atmosphere of air or oxygen-containing gas.

In the invention, each of a cyclopentadiene derivative and an aliphatic lower alcohol can be introduced to the catalyst layer in the form of a liquid, gas or a mixture of a liquid and gas. Further, it is preferable to supply nitrogen, helium, argon or like inert gas, water vapor, a small amount of air or oxygen, to enhance the activity of the catalyst and extend a catalyst life. The reaction zone is maintained usually at a temperature of 200° to 700° C., preferably at 400° to 550° C. With too low in the reaction temperature, the reaction velocity become slow, and with too high in the reaction temperature, side reactions occurs, both not preferable in economical points. The reaction is conducted preferably at normal pressure but can be carried out at an increased or reduced pressure. The reaction may proceed in batchwise or continuous process and are conducted in various processes which are adoptable to vapor-phase reaction. Selectivity of the resulting alkylcyclopentadiene derivatives, for example, proportions of monoalkylated, dialkylated, trialkylated, tetraalkylated derivative and the like can be varied depending on the reaction conditions such as kinds and methods of preparation of the catalyst, molar ratio of the starting cyclopentadiene derivative and aliphatic lower alcohol, reaction temperature, feed velocity of the starting materials to the catalyst layer or the like.

The invention will be described with reference to the following examples.

EXAMPLE 1

To a mixture of 130 g of calcium hydroxide and 2 g of γ-alumina powder (80 to 100μ) was added about 500 ml of water. The mixture was thoroughly admixed and dried at 110° C. for 10 to 15 hours to prepare a catalyst. The catalyst was pulverized to a powder having particle size of 5 to 9 mesh (this method is hereinafter referred to as "Method-1"). The powdery catalyst was calcined at 500° C. for 3 hours with introducing nitrogen gas at a velocity of 30 ml/min.

The followings are methods of preparation of the catalyst shown in the column (*) of the later Tables.

Method-1; Water is added to a catalytic compound and the mixture is admixed and dried at 110° C. The resulting solid is pulverized to prepare a powder.

Method-2; A catalytic compound is subjected to compression molding and pulverized to prepare a powder.

Method-3; A pulverized catalyst is impregnated with an aqueous solution or dispersion of another catalyst and then dried.

The reaction was conducted with use of a usual reaction apparatus of a fixed-bed flow method. The reaction tube is made of quartz glass and is one meter in long and 30 mm in inner diameter. The reaction tube was packed with 50 g of the calcined catalyst and the catalyst was further calcined at 500° C. for 3 hours while introducing nitrogen gas at a velocity of 30 ml/min. Then, the reaction zone was heated to 450° C. and thereto were introduced 0.1 mole of cyclopentadiene and 0.5 mole of methanol over a period of 5 hours with use of microfeeder. The reaction product was trapped by use of dry ice-acetone bath and was analysed by gas-chromatography.

Conversions of methanol and cyclopentadiene were 95% and 60.4% respectively. Selectivities of alkylcyclopentadienes are 37.3% in monomethylated derivative, 15.9% in dimethylated derivative and 2.6% in trimethylated derivative. Conversion of the starting materials and selectivity of alkylcyclopentadiene were given by the following equations.

$$\text{Conversion (\%)} = \left(100 - \frac{\text{mole of recovered starting material}}{\text{mole of supplied starting material}}\right) \times 100$$

$$\text{Selectivity (\%)} = \frac{\text{mole of produced alklycyclopentadiene}}{\text{mole of converted cyclopentadiene}} \times 100$$

EXAMPLES 2 TO 25

The reactions of cyclopentadiene and methanol were conducted in the same manner as in Example 1 with use of various catalysts listed in Table 1. The results were shown in Table 1.

In Example 3, to the reaction zone was added 3.06 g of water.

EXAMPLES 26 TO 62

The reactions of methylcyclopentadiene and methanol were conducted in the same manner as in Example 1 with use of various catalysts listed in Table 2. The results were shown in Table 2.

EXAMPLES 63 TO 66

In the Table,

Molar ratio is a value of (mole of used cyclopentadiene derivative)/(mole of used alcohol).

W/F is a value of (catalyst amount, g)/(feed velocity of starting material, mole/hr).

A: cyclopentadiene,
B: monomethylated derivative,
C: dimethylated derivative,
D: trimethylated derivative,
E: methylcyclopentadiene,
F: tetramethylated derivative,
G: monoalkylated derivative,
H: dialkylated derivative,
I: trialkylated derivative Alumina sol used in Tables 1 and 2 contains 7% by weight of alumina stabilized by carboxylic acid. Figures in parentheses indicate the solid weight of alumina contained in the sol.

TABLE 1

| Ex. | Catalyst (g) | (*) | Molar ratio | Temp (°C.) | W/F | Conv (%) Methanol | A | Selec (%) B | C | D |
|---|---|---|---|---|---|---|---|---|---|---|
| 2 | Ca(OH)$_2$(130)—alumina sol(2) | 1 | 0.1/0.5 | 450 | 257 | 95.8 | 54.1 | 50.5 | 18.4 | 2.9 |
| 3 | Ca(OH)$_2$(130)—alumina sol(2) | 1 | 0.1/0.5 | 450 | 257 | 95.2 | 50.2 | 61.8 | 28.7 | 5.5 |
| 4 | Ca(OH$_2$(130)—alummina sol(2) | 2 | 0.1/0.5 | 450 | 257 | 90.5 | 59.9 | 25.7 | 7.9 | 1.7 |
| 5 | NaOH(6)—alumina beads(100) | 3 | 0.1/0.5 | 450 | 257 | 33.0 | 38.0 | 52.4 | 5.6 | — |
| 6 | KOH(12)—alumina beads(100) | 3 | 0.1/0.5 | 450 | 257 | 54.5 | 39.5 | 39.7 | 14.1 | — |
| 7 | Mg(OH)$_2$(12)—alumina beads(100) | 3 | 0.1/0.5 | 450 | 257 | 81.3 | 36.2 | 28.7 | — | — |
| 8 | Ca(OH$_2$(14)—alumina beads(100) | 3 | 0.1/0.5 | 450 | 257 | 96.9 | 87.6 | 21.9 | 15.3 | 4.2 |
| 9 | NaOH(6)—Ca(OH)$_2$(14)—alumina beads(100) | 3 | 0.1/0.5 | 450 | 257 | 99.9 | 63.7 | 38.0 | 15.0 | 2.0 |
| 10 | Ca(OH)$_2$(130)—ZnO(1.6) | 1 | 0.1/0.5 | 450 | 120 | 99.8 | 61.5 | 35.8 | 11.9 | — |
| 11 | Ca(OH)$_2$(130)—CrO$_3$(2) | 1 | 0.1/0.5 | 450 | 120 | 99.5 | 80.2 | 18.2 | 7.9 | 1.5 |
| 12 | Ca(OH)$_2$(130)—Cr$_2$O$_3$(3) | 1 | 0.1/0.5 | 450 | 120 | 99.3 | 74.7 | 25.4 | 13.4 | 2.9 |
| 13 | Ca(OH)$_2$(130)—B$_2$O$_3$(1.4) | 1 | 0.1/0.5 | 450 | 120 | 98.6 | 68.5 | 20.4 | 7.2 | 1.2 |
| 14 | Ca(OH)$_2$(130)—CuO(1.6) | 1 | 0.1/0.5 | 450 | 120 | 96.9 | 69.7 | 28.8 | 13.3 | 2.7 |
| 15 | Ca(OH)$_2$(128)—Cu$_2$O(2.8) | 1 | 0.1/0.5 | 450 | 120 | 96.6 | 78.7 | 19.9 | 9.0 | 1.8 |
| 16 | Ca(OH)$_2$(130)—NiO(1.4) | 1 | 0.1/0.5 | 450 | 120 | 99.9 | 91.3 | 6.6 | 3.1 | 0.7 |
| 17 | Ca(OH)$_2$(128)—Ni$_2$O$_3$(3.2) | 1 | 0.1/0.5 | 450 | 120 | 99.6 | 87.7 | 8.1 | 4.4 | 1.4 |
| 18 | Ca(OH)$_2$(126)—(CH$_3$COO)$_2$Mn(4.6) | 1 | 0.1/1.0 | 450 | 120 | 99.2 | 74.8 | 16.6 | 5.6 | 0.9 |
| 19 | Ca(OH)$_2$(128)—Fe$_2$O$_3$(3.0) | 1 | 0.1/1.0 | 450 | 120 | 97.8 | 69.2 | 16.0 | 3.6 | 0.3 |
| 20 | Ca(OH)$_2$(130)—FeO(OH)(1.8) | 1 | 0.1/1.0 | 450 | 120 | 99.8 | 57.0 | 17.4 | 2.5 | 0.2 |
| 21 | Ca(OH)$_2$(130)—FeO(2.4) | 1 | 0.1/1.0 | 450 | 120 | 99.8 | 75.5 | 16.3 | 4.8 | 0.6 |
| 22 | Ca(OH)$_2$(126)—Fe$_3$O$_4$(4.4) | 1 | 0.1/1.0 | 450 | 120 | 99.9 | 62.0 | 13.3 | 1.8 | 1.3 |
| 23 | Ca(OH)$_2$(130)—TiO$_2$(1.6) | 1 | 0.1/1.0 | 450 | 120 | 99.8 | 58.3 | 22.0 | 5.1 | — |
| 24 | Ca(OH)$_2$(130)—alumina sol(2) | 1 | 0.1/1.0 | 300 | 455 | 80.5 | 25.9 | 17.1 | 3.7 | 0.3 |
| 25 | Ca(OH)$_2$(130)—alumina sol(2) | 1 | 0.1/1.0 | 250 | 455 | 75.3 | 10.2 | 23.3 | — | — |

The reactions of cyclopentadiene and aliphatic lower alcohol were conducted in the same manner as in Example 1. The results were given in Table 3.

TABLE 2

| Ex. | Catalyst (g) | (*) | Molar ratio | Temp (°C.) | W/F | Conv (%) Methanol | E | Selec (%) C | D | F |
|---|---|---|---|---|---|---|---|---|---|---|
| 26 | Ca(OH)$_2$(130) | 1 | 0.1/0.5 | 450 | 120 | 99.7 | 57.6 | 18.2 | 0.8 | — |
| 27 | Ca(OH)$_2$(132)—alumiina sol(1) | 1 | 0.1/1.0 | 450 | 120 | 99.4 | 54.0 | 34.1 | 5.3 | 0.2 |
| 28 | Ca(OH)$_2$(130)—SiO$_2$(9) | 1 | 0.1/1.0 | 450 | 120 | 99.7 | 59.9 | 27.5 | 4.9 | 0.3 |
| 29 | Ca(OH)$_2$(128)—P$_2$O$_5$(2.8) | 1 | 0.1/1.0 | 450 | 120 | 99.8 | 34.9 | 46.1 | 4.2 | — |
| 30 | Ca(OH)$_2$(130)—MnO$_2$(1.8) | 1 | 0.1/1.0 | 450 | 120 | 98.1 | 86.5 | 7.6 | 1.3 | — |
| 31 | Na$_2$CO$_3$(184)—alumina sol(20) | 1 | 0.1/1.0 | 400 | 125 | 99.8 | 20.0 | 88.5 | 10.8 | — |
| 32 | K$_2$CO$_3$(179)—alumina sol(20) | 1 | 0.1/0.3 | 450 | 229 | 83.0 | 66.5 | 34.1 | 11.1 | 1.4 |
| 33 | Ca(OH)$_2$(130)—LiOH.H$_2$O(0.8) | 1 | 0.1/1.0 | 450 | 120 | 99.8 | 16.7 | 34.3 | — | — |
| 34 | Ca(OH)$_2$(130)—Be(OH)$_2$(0.8) | 1 | 0.1/1.0 | 450 | 120 | 99.8 | 44.1 | 39.0 | 5.0 | — |
| 35 | Ca(OH)$_2$(130)—Co(OH)$_2$(1.8) | 1 | 0.1/1.0 | 450 | 120 | 99.8 | 92.2 | 4.5 | 1.0 | — |
| 36 | Na$_2$CO$_3$(20)—alumina beads(85) | 3 | 0.1/0.1 | 400 | 79.5 | 92.8 | 65.7 | 37.4 | 8.3 | — |
| 37 | NaOH(0.8)—alumina beads(120) | 3 | 0.3/0.3 | 550 | 132 | 90.0 | 66.9 | 6.4 | 1.3 | — |
| 38 | Ca(OH)$_2$(128)—Ga$_2$O$_3$(7) | 1 | 0.1/1.0 | 450 | 120 | 98.9 | 72.1 | 25.9 | 7.8 | 0.7 |
| 39 | Ca(OH)$_2$(128)—Sc$_2$O$_3$(3.6) | 1 | 0.1/1.0 | 450 | 120 | 98.6 | 41.6 | 41.3 | 4.5 | — |
| 40 | Ca(OH)$_2$(130)—GeO$_2$(1.8) | 1 | 0.1/1.0 | 450 | 120 | 99.8 | 50.9 | 32.0 | 3.9 | — |
| 41 | Ca(OH)$_2$(130)—SeO$_2$(1.8) | 1 | 0.1/1.0 | 450 | 120 | 99.4 | 91.6 | 4.0 | 0.7 | — |
| 42 | Ca(OH)$_2$(128)—V$_2$O$_3$(3.6) | 1 | 0.1/1.0 | 450 | 120 | 99.8 | 59.2 | 29.4 | 4.4 | — |
| 43 | Ca(OH)$_2$(128)—V$_2$O$_5$(3.6) | 1 | 0.1/1.0 | 450 | 120 | 99.8 | 56.0 | 30.2 | 4.6 | — |
| 44 | Mg(OH)$_2$(190) | 1 | 0.1/0.3 | 450 | 87.5 | 99.8 | 91.0 | 6.4 | — | — |
| 45 | Mg(OH)$_2$(198)—alumina sol(1) | 1 | 0.1/0.3 | 450 | 292 | 99.8 | 96.0 | 15.0 | 0.5 | — |
| 46 | Ca(OH)$_2$(130)—BaO(1) | 1 | 0.1/1.0 | 450 | 120 | 99.7 | 60.5 | 30.6 | 8.8 | 0.7 |
| 47 | Ca(OH)$_2$(132)—Al(0.6) | 1 | 0.1/1.0 | 450 | 120 | 99.8 | 46.4 | 42.9 | 6.1 | — |
| 48 | Ca(OH)(130)—Ca(1.6) | 1 | 0.1/1.0 | 450 | 120 | 99.8 | 47.9 | 41.8 | 6.0 | — |
| 49 | Ca(OH)(130)—Na(0.8) | 1 | 0.1/1.0 | 450 | 120 | 99.8 | 49.1 | 50.9 | 2.1 | — |

TABLE 2-continued

| Ex. | Catalyst (g) | (*) | Molar ratio | Temp (°C.) | W/F | Conv (%) Methanol | E | Selec (%) C | D | F |
|---|---|---|---|---|---|---|---|---|---|---|
| 50 | Ca(OH)$_2$(132)—Mg(1) | 1 | 0.1/1.0 | 450 | 120 | 99.8 | 58.0 | 30.7 | 4.7 | — |
| 51 | Ca(OH)$_2$(132)—active carbon(0.4) | 1 | 0.1/1.0 | 450 | 120 | 99.7 | 54.7 | 37.7 | 6.3 | 0.3 |
| 52 | Ca(OH)$_2$(130)—Cu(2.6) | 1 | 0.1/1.0 | 450 | 120 | 99.8 | 87.9 | 11.1 | 5.4 | 0.7 |
| 53 | Ca(OH)$_2$(130)—Zn(2.6) | 1 | 0.1/1.0 | 450 | 120 | 99.8 | 74.6 | 25.2 | 7.0 | 0.5 |
| 54 | Ca(OH)$_2$(130)—Ti(2.4) | 1 | 0.1/1.0 | 450 | 120 | 99.7 | 47.9 | 41.3 | 5.8 | 0.2 |
| 55 | Ca(OH)$_2$(130)—Ni(1.2) | 1 | 0.1/1.0 | 450 | 120 | 99.9 | 81.6 | 12.0 | 2.5 | 0.2 |
| 56 | Ca(OH)$_2$(130)—Cr(2) | 1 | 0.1/1.0 | 450 | 120 | 99.8 | 41.1 | 38.9 | 2.2 | — |
| 57 | Ca(OH)$_2$(130)—Mn(2.2) | 1 | 0.1/1.0 | 450 | 120 | 99.6 | 38.5 | 44.4 | 4.5 | — |
| 58 | Ca(OH)$_2$(130)—Co(2.4) | 1 | 0.1/1.0 | 450 | 120 | 99.7 | 68.4 | 15.5 | 1.9 | — |
| 59 | Sr(OH)$_2$.8H$_2$O(150) | 1 | 0.1/0.3 | 450 | 52.5 | 47.5 | 58.0 | 21.9 | 4.9 | 0.5 |
| 60 | Ca(OH)$_2$(130)—Fe(1.2) | 1 | 0.1/1.0 | 450 | 120 | 99.3 | 56.0 | 33.6 | 5.6 | — |
| 61 | Ca(OH)$_2$(130)—alumina sol(2) | 1 | 0.1/1.0 | 300 | 455 | 79.6 | 5.1 | 17.8 | — | — |
| 62 | Na$_2$CO$_3$(100)—KOH(2) | 1 | 0.1/1.0 | 450 | 106 | 23.4 | 40.6 | 20.5 | — | — |

TABLE 3

| Ex. | Alcohol | (*) | Molar ratio | Temp (°C.) | W/F | Conv (%) Alcohol | A | Selec (%) G | H | I |
|---|---|---|---|---|---|---|---|---|---|---|
| 63 | ethanol | 1 | 0.1/0.5 | 450 | 455 | 91.6 | 53.4 | 11.4 | — | — |
| 64 | n-propanol | 1 | 0.1/0.5 | 450 | 455 | 81.4 | 45.9 | 10.8 | 7.3 | — |
| 65 | i-propanol | 1 | 0.1/0.5 | 450 | 455 | 79.4 | 49.4 | 3.2 | 1.7 | — |
| 66 | n-butanol | 1 | 0.1/0.5 | 450 | 455 | 89.0 | 87.9 | 0.8 | — | — |

EXAMPLE 67

To a mixture of 130 g of calcium hydroxide, 10 g of sodium hydroxide and 5 g of Sb$_2$O$_3$ powder was added about 500 ml of water. The mixture was thoroughly admixed and dried at 110° C. for 10 to 15 hours to prepare a catalyst. The catalyst was pulverized to a powder having particle size of 5 to 9 mesh. The powdery catalyst was calcined at 500° C. for 3 hours with introducing nitrogen gas at a velocity of 30 ml/min.

The reaction was conducted in the same manner as in Example 1.

Conversions of methanol and cyclopentadiene were 96% and 71.1% respectively. Selectivities of alkylcyclopentadienes are 40.5% in monomethylated derivative, 18.3% in dimethylated derivative and 4.0% in trimethylated derivative.

EXAMPLES 68 TO 76

The reactions of cyclopentadiene and methanol were conducted in the same manner as in Example 67 with use of various catalysts listed in Table 4. The results were shown in Table 4.

EXAMPLES 77 TO 85

The reactions of methylcyclopentadiene and methanol were conducted in the same manner as in Example 67 with use of various catalysts listed in Table 5. The results were shown in Table 5.

EXAMPLES 86 TO 103

The reaction of cyclopentadiene and methanol was conducted with use of a pulse reaction system. Prior to the reaction, distribution or amounts of products was confirmed to resemble to those in the flow process.

The reaction tube is made of quartz glass and is 110 mm in long and 6 mm in inner diameter. The reaction tube was packed with 0.8 g of the calcined catalyst having a particle size of 16 to 20 mesh and the catalyst was further calcined at 500° C. for 30 minutes while introducing nitrogen gas at a velocity of 40 ml/min. Thereto were introduced the starting materials at a prescribed temperature by use of microsyringes. As one pulse was used 1 μl of a mixture of 0.1 mole of a cyclopentadiene derivative, 1 mole of alcohol and 0.5 g of toluene as an internal standard used for quantitative analysis. The products were directly introduced to a connected gas-chromatography and analysed. The results were given in Table 6.

EXAMPLES 104 TO 134

The reactions of methylcyclopentadiene and methanol were conducted in the same manner as in Examples 86 to 103 with use of various catalysts listed in Table 7. The results were shown in Table 7.

TABLE 4

| Ex. | Catalyst (g) | (*) | Molar ratio | Temp (°C.) | W/F | Conv (%) Methanol | A | Selec (%) B | C | D |
|---|---|---|---|---|---|---|---|---|---|---|
| 68 | NaOH(50)—WO$_3$(%)—alumina beads (100) | 3 | 0.1/1.0 | 450 | 120 | 91.2 | 80.5 | 55.3 | 29.0 | 5.1 |
| 69 | Ca(OH)$_2$(130)—NaOH(10)—In$_2$O$_3$(5) | 1 | 0.1/1.0 | 450 | 120 | 90.8 | 77.0 | 47.9 | 12.1 | 2.2 |
| 70 | Ca(OH)$_2$(130)—KOH(10)—Sb$_2$O$_3$(5) | 1 | 0.1/1.0 | 450 | 120 | 88.7 | 68.0 | 51.7 | 22.3 | 4.6 |
| 71 | Ca(OH)$_2$(130)—Y(2) | 1 | 0.5/1.0 | 450 | 200 | 95.6 | 89.7 | 46.2 | 13.7 | 0.9 |
| 72 | Ca(OH)$_2$(130)—NaOH(10)—ZrO$_2$(3) | 1 | 0.5/1.0 | 450 | 120 | 85.0 | 60.3 | 48.3 | 12.6 | 1.1 |
| 73 | Ca(OH)$_2$(130)—MoO$_2$(3) | 1 | 0.5/1.0 | 500 | 120 | 88.7 | 87.1 | 42.0 | 11.9 | 2.1 |
| 74 | Ca(OH)$_2$(130)—SnO$_2$(3) | 1 | 0.1/1.0 | 450 | 120 | 90.3 | 78.2 | 40.8 | 12.5 | 1.0 |
| 75 | NaOH(50)—Sn(3)—active carbon particle(100) | 3 | 0.1/1.0 | 400 | 120 | 80.1 | 69.8 | 43.5 | 16.7 | 3.6 |
| 76 | Ca(OH)$_2$(130)—Na$_2$CO$_3$(10)— | 1 | 0.1/1.0 | 400 | 120 | 93.5 | 71.9 | 35.6 | 9.8 | 0.8 |

TABLE 4-continued

| Ex. | Catalyst (g) | (*) | Molar ratio | Temp (°C.) | W/F | Conv (%) Methanol | A | Selec (%) B | C | D |
|---|---|---|---|---|---|---|---|---|---|---|
| | CeO$_2$(5)—V$_2$O$_3$(4) | | | | | | | | | |

TABLE 5

| Ex. | Catalyst (g) | (*) | Molar ratio | Temp (°C.) | W/F | Conv (%) Methanol | E | Selec (%) C | D | F |
|---|---|---|---|---|---|---|---|---|---|---|
| 77 | Ca(OH)$_2$(130)—KOH(10)—RuO$_2$(5)—MnO$_2$(2) | 1 | 0.5/1.0 | 450 | 120 | 85.0 | 66.1 | 35.6 | 19.9 | 4.0 |
| 78 | Ca(OH)$_2$(130)NaOH(10)—Ir$_2$O$_3$(5)—CrO$_3$(2) | 1 | 0.5/1.0 | 450 | 200 | 90.5 | 75.6 | 36.7 | 20.1 | 3.5 |
| 79 | Ca(OH)$_2$(130)—LiOH(10)—La(CO$_3$)$_3$(5)—Fe$_2$O$_3$(3) | 1 | 0.5/1.0 | 450 | 150 | 98.5 | 85.1 | 41.2 | 18.3 | 4.6 |
| 80 | Mg(OH)$_2$(130)—NaOH(20)—Cs$_2$O(5)—CuO(3) | 1 | 0.5/1.0 | 450 | 120 | 95.6 | 77.9 | 37.1 | 16.7 | 2.3 |
| 81 | Ca(OH)$_2$(130)—NaOH(10)—Ho$_2$O$_3$(5)—Ni$_2$O$_3$(3) | 1 | 0.1/1.0 | 450 | 120 | 89.5 | 81.0 | 35.0 | 13.5 | 0.8 |
| 82 | Ca(OH)$_2$(130)—KOH(10)—Ag(5)—ZnO(3) | 1 | 0.1/1.0 | 450 | 120 | 99.8 | 70.7 | 37.2 | 16.7 | 1.9 |
| 83 | KOH(50)—Rh(3)—graphite(100) | 3 | 0.1/1.0 | 450 | 120 | 87.8 | 67.4 | 40.2 | 10.5 | 1.3 |
| 84 | Ca(OH)$_2$(130)—Nd$_2$O$_3$(6) | 1 | 0.1/1.0 | 450 | 120 | 93.5 | 83.5 | 38.7 | 16.0 | 1.0 |
| 85 | Ca(OH)$_2$(130)—NaOH(10)—Pd(5)—TiO$_2$(2) | 1 | 0.1/1.0 | 450 | 120 | 90.4 | 71.3 | 36.6 | 17.1 | 3.2 |

TABLE 6

| Ex. | Catalyst (g) | (*) | Temp (°C.) | Conv (%) Methanol | A | Selec (%) B | C | D |
|---|---|---|---|---|---|---|---|---|
| 86 | Ca(OH)$_2$(64.8)—Zr(0.897) | 1 | 500 | 100 | 46.2 | 42.6 | 10.5 | — |
| 87 | Ca(OH)$_2$(64.8)—Nb(0.914) | 1 | 500 | 100 | 62.5 | 32.0 | 12.1 | 2.3 |
| 88 | Ca(OH)$_2$(64.2)—MoO$_3$(1.40) | 1 | 500 | 100 | 58.9 | 29.7 | 9.0 | 1.4 |
| 89 | Ca(OH)$_2$(64.0)—Zr(OH)$_4$(1.55) | 1 | 500 | 99.8 | 13.0 | 89.2 | 10.8 | — |
| 90 | Ca(OH)$_2$(62.0)—La$_2$O$_3$(3.16) | 1 | 500 | 99.8 | 38.8 | 48.5 | 10.5 | 0.6 |
| 91 | Ca(OH)$_2$(63.0)—Ag$_2$O(2.22) | 1 | 500 | 100 | 64.6 | 34.1 | 13.9 | 2.6 |
| 92 | Ca(OH)$_2$(64.4)—NaOH(5)—Te(1.25) | 1 | 500 | 100 | 96.8 | 20.5 | 12.4 | 0.9 |
| 93 | Ca(OH)$_2$(8.2)—Tb$_4$O$_7$(0.931) | 1 | 500 | 100 | 72.1 | 10.7 | 2.7 | — |
| 94 | Ca(OH)$_2$(15.3)—Tm$_2$O$_3$(0.897) | 1 | 500 | 100 | 27.1 | 66.1 | 12.1 | — |
| 95 | Ca(OH)$_2$(57.8)—KOH(5)—Ce$_2$(C$_2$O$_4$)$_3$.9H$_2$O(6.20) | 1 | 500 | 100 | 58.3 | 32.8 | 16.5 | 1.3 |
| 96 | Ca(OH)$_2$(63.7)—W(1.78) | 1 | 400 | 90.1 | 35.6 | 57.2 | 10.1 | 0.5 |
| 97 | Ca(OH)$_2$(60.6)—Ta$_2$O$_5$(4.07) | 1 | 500 | 100 | 38.3 | 52.2 | 12.6 | 1.4 |
| 98 | Ca(OH)$_2$(31.8)—Ir(0.927) | 1 | 500 | 99.6 | 56.9 | 32.5 | 10.5 | 1.6 |
| 99 | Ca(OH)$_2$(21.0)—PtO$_2$.H$_2$O(0.780) | 1 | 450 | 95.2 | 75.4 | 12.1 | 5.6 | 0.9 |
| 100 | Ca(OH)$_2$(25.3)—HfO$_2$(0.809) | 1 | 500 | 100 | 28.5 | 63.2 | 10.9 | — |
| 101 | Ca(OH)$_2$(31.8)—Os(0.918) | 1 | 500 | 98.7 | 15.5 | 89.0 | 11.0 | — |
| 102 | Ca(OH)$_2$(64.1)—Cd(OH)$_2$(1.43) | 1 | 500 | 99.7 | 76.4 | 11.9 | 3.7 | — |
| 103 | Ca(OH)$_2$(63.4)—Bi(2.01) | 1 | 500 | 99.6 | 70.6 | 30.3 | 16.9 | 4.1 |

TABLE 7

| Ex. | Catalyst (g) | (*) | Temp (°C.) | Conv (%) Methanol | E | Selec (%) C | D | F |
|---|---|---|---|---|---|---|---|---|
| 104 | Ca(OH)$_2$(63.1)—Y$_2$O$_3$(2.16) | 1 | 500 | 99.6 | 71.1 | 28.1 | 6.7 | 0.5 |
| 105 | Ca(OH)$_2$(62.7)—Nb$_2$O$_5$(2.53) | 1 | 500 | 98.7 | 73.7 | 29.3 | 7.9 | 0.6 |
| 106 | Ca(OH)$_2$(64.8)—Mo(0.943) | 1 | 500 | 100 | 78.2 | 22.6 | 6.6 | 0.7 |
| 107 | Ca(OH)$_2$(64.7)—Ru(0.992) | 1 | 500 | 99.7 | 75.4 | 32.4 | 10.3 | 1.0 |
| 108 | Ca(OH)$_2$(64.3)—SnO(1.31) | 1 | 500 | 99.6 | 77.6 | 29.3 | 9.8 | 0.9 |
| 109 | Ca(OH)$_2$(32.2)—PdO(0.522) | 1 | 500 | 99.6 | 87.9 | 16.3 | 7.2 | 1.0 |
| 110 | Ca(OH)$_2$(64.5)—In(1.12) | 1 | 500 | 99.6 | 75.9 | 30.6 | 9.5 | 0.8 |
| 111 | Ca(OH)$_2$(64.4)—Sb(1.19) | 1 | 500 | 99.6 | 77.3 | 24.7 | 7.7 | 0.8 |
| 112 | Ca(OH)$_2$(64.0)—TeO$_2$(1.55) | 1 | 500 | 100 | 94.1 | 9.6 | 4.3 | 0.5 |
| 113 | Ca(OH)$_2$(15.5)—Pr$_2$O$_3$(0.775) | 1 | 500 | 99.5 | 91.6 | 7.6 | 2.2 | 0.3 |
| 114 | Ca(OH)$_2$(15.4)—Sm$_2$O$_3$(0.817) | 1 | 500 | 99.5 | 71.6 | 28.9 | 6.7 | 0.5 |
| 115 | Ca(OH)$_2$(15.4)—Eu$_2$O$_3$(0.823) | 1 | 500 | 99.5 | 71.6 | 32.0 | 8.9 | 0.8 |
| 116 | Ca(OH)$_2$(15.4)—Gd$_2$O$_3$(0.847) | 1 | 500 | 99.6 | 66.1 | 34.2 | 7.1 | 0.5 |
| 117 | Ca(OH)$_2$(15.3)—Er$_2$O$_3$(0.890) | 1 | 500 | 99.5 | 76.4 | 27.5 | 0.9 | 0.9 |
| 118 | Ca(OH)$_2$(15.4)—Dy$_2$O$_3$(0.869) | 1 | 500 | 99.4 | 63.3 | 39.0 | 9.2 | 0.7 |
| 119 | Ca(OH)$_2$(15.3)—Yb$_2$O$_3$(0.915) | 1 | 500 | 99.4 | 68.8 | 34.3 | 9.2 | 0.8 |
| 120 | Ca(OH)$_2$(61.8)—Ce(CH$_3$CO$_2$)$_3$(3.15) | 1 | 500 | 99.4 | 80.1 | 16.1 | 4.9 | 0.6 |
| 121 | Ca(OH)$_2$(63.4)—Ce(OH)$_3$(2.00) | 1 | 500 | 99.6 | 71.1 | 27.0 | 5.7 | 0.4 |
| 122 | Ca(OH)$_2$(59.5)—Ce$_2$(CO$_3$)$_3$.5H$_2$O(4.97) | 1 | 500 | 99.2 | 90.1 | 9.7 | 3.0 | 0.3 |
| 123 | Ca(OH)$_2$(31.8)—Re(0.900) | 1 | 500 | 100 | 85.3 | 18.2 | 5.9 | 0.6 |
| 124 | Ca(OH)$_2$(64.1)—CsOH(1.46) | 1 | 500 | 99.3 | 65.8 | 31.0 | 5.8 | 0.4 |
| 125 | Ca(OH)$_2$(62.0)—Cs$_2$CO$_3$(3.06) | 1 | 500 | 99.5 | 74.4 | 23.8 | 5.0 | 0.4 |
| 126 | Ca(OH)$_2$(31.9)—Hf(0.863) | 1 | 500 | 99.5 | 63.0 | 38.4 | 8.3 | 0.5 |

TABLE 7-continued

| Ex. | Catalyst (g) | Temp (*) | (°C.) | Conv (%) Methanol | Selec (%) E | C | D | F |
|---|---|---|---|---|---|---|---|---|
| 127 | Ca(OH)$_2$(62.2)—Th(OH)$_4$(2.84) | 1 | 500 | 99.5 | 41.3 | 42.4 | 5.2 | — |
| 128 | Ca(OH)$_2$(14.3)—OsO$_4$(0.550) | 1 | 500 | 98.7 | 90.5 | 10.6 | 4.3 | 0.7 |
| 129 | Ca(OH)$_2$(64.6)—Cd(1.10) | 1 | 500 | 99.5 | 83.0 | 18.2 | 5.9 | 0.6 |
| 130 | Ca(OH)$_2$(64.6)—CdO(1.25) | 1 | 500 | 99.5 | 90.5 | 10.5 | 4.2 | 0.6 |
| 131 | Ca(OH)$_2$(63.8)—CdCO$_3$(1.67) | 1 | 500 | 99.5 | 88.9 | 12.3 | 5.2 | 0.5 |
| 132 | Ca(OH)$_2$(62.7)—Bi(OH)$_3$(2.48) | 1 | 500 | 99.2 | 94.2 | 6.9 | 2.7 | 0.3 |
| 133 | Ca(OH)$_2$(60.5)—NaOH(5)—Tl$_2$O$_3$(4.19) | 1 | 500 | 99.0 | 80.5 | 15.5 | 4.3 | 0.4 |
| 134 | Ca(OH)$_2$(63.4)—NaOH(5)—Pb(1.99) | 1 | 500 | 99.2 | 85.5 | 13.8 | 6.7 | 0.7 |

EXAMPLE 135

Potassium carbonate powder having a particle size of 20 to 60 mesh calcined at 500° C. for 3 hours with introducing nitrogen gas at a velocity of 30 ml/min.

The reaction was conducted with use of the same reaction apparatus in Example 1. The reaction tube was packed with 50 g of the calcined catalyst and the catalyst was further calcined at 500° C. for 3 hours while introducing nitrogen gas at a velocity of 30 ml/min. Then, the reaction zone was heated to 500° C. and thereto were introduced 0.1 mole of methylcyclopentadiene and 1.0 mole of methanol over a period of 2 hours with use of microfeeder. The reaction product was trapped by use of dry ice-acetone bath and was analysed by gas-chromatography.

Conversions of methanol and methylcyclopentadiene were 51.3% and 57.6% respectively. Selectivities of alkylcyclopentadienes are 14.4% in dimethylated derivative and 1.43% in trimethylated derivative.

EXAMPLES 136 TO 141

The reactions of cyclopentadiene and methanol were conducted in the same manner as in Example 135 with use of various catalysts listed in Table 8. The results were shown in Table 8.

EXAMPLES 142 TO 148

The reactions of methylcyclopentadiene and methanol were conducted in the same manner as in Example 135 with use of various catalysts listed in Table 9. The results were shown in Table 9.

EXAMPLES 149 TO 152

The reaction of cyclopentadiene and methanol was conducted with use of a pulse reaction system in the same manner as in Examples 86 to 103. The results were given in Table 10.

EXAMPLES 153 TO 157

The reactions of methylcyclopentadiene and methanol were conducted in the same manner as in Examples 149 to 152 with use of various catalysts listed in Table 11. The results were shown in Table 11.

As shown in Tables 8 to 11, it is available to introduce one alkyl group into cyclopentadiene ring selectively by the use of basic catalyst having H— of 7.1 to 17.2.

EXAMPLES 158 AND 159

The reaction of cyclopentadiene dimer or methylcyclopentadiene dimer with methanol was conducted in the same manner as in Example 1 with use of a catalyst shown in Table 12. The results were given in Table 12.

TABLE 8

| Ex. | Catalyst (g) | Molar ratio | Temp (°C.) | W/F | Conv (%) Methanol | A | B | C | D |
|---|---|---|---|---|---|---|---|---|---|
| 136 | Na$_2$CO$_3$ (50) | 0.1/1.0 | 450 | 87.1 | 31.2 | 34.8 | 33.0 | 2.96 | — |
| 137 | K$_2$CO$_3$ (50) | 0.1/1.0 | 450 | 87.1 | 32.8 | 31.4 | 27.8 | 1.96 | — |
| 138 | Na$_3$PO$_4$ (50) | 0.1/1.0 | 450 | 87.1 | 80.5 | 94.9 | 8.00 | 4.74 | 0.609 |
| 139 | NaAlO$_2$ (50) | 0.1/1.0 | 450 | 87.1 | 50.3 | 76.7 | 11.0 | 1.09 | — |
| 140 | CaWO$_4$ (20) | 0.04/0.4 | 500 | 90.9 | 67.3 | 94.5 | 13.5 | 7.30 | 1.01 |
| 141 | Na$_2$MoO$_4$ (20) | 0.1/1.0 | 450 | 36.4 | 38.4 | 24.2 | 21.3 | 1.17 | — |

TABLE 9

| Ex. | Catalyst (g) | Molar ratio | Temp (°C.) | W/F | Conv (%) Methanol | E | C | D | F |
|---|---|---|---|---|---|---|---|---|---|
| 142 | Na$_2$CO$_3$ (50) | 0.1/1.0 | 500 | 83.3 | 49.7 | 56.5 | 10.5 | 0.431 | — |
| 143 | K$_2$CO$_3$ (50) | 0.1/1.0 | 450 | 87.1 | 51.6 | 51.5 | 7.44 | — | — |
| 144 | Na$_3$PO$_4$ (50) | 0.1/1.0 | 450 | 87.1 | 74.8 | 84.4 | 12.1 | 1.06 | — |
| 145 | NaAlO$_2$ (50) | 0.1/1.0 | 450 | 87.1 | 57.8 | 72.5 | 10.9 | 0.400 | — |
| 146 | CaWO$_4$ (20) | 0.04/0.4 | 500 | 56.9 | 87.1 | 90.6 | 10.5 | 0.431 | — |
| 147 | Na$_2$MoO$_4$ (20) | 0.1/1.0 | 450 | 87.1 | 24.7 | 43.1 | 7.05 | — | — |
| 148 | Na$_2$SnO$_3$ (50) | 0.1/1.0 | 500 | 87.1 | 82.7 | 58.4 | 17.3 | 1.32 | — |

TABLE 10

| Ex. | Catalyst (g) | Temp (°C.) | Conv (%) Methanol | A | B | C | D |
|---|---|---|---|---|---|---|---|
| 149 | K$_2$WO$_4$ (2) | 500 | 75.9 | 71.5 | 28.4 | — | — |
| 150 | MgWO$_4$ (1) | 500 | 72.5 | 96.8 | 59.7 | 9.9 | 2.33 |
| 151 | CaMoO$_4$ (1) | 500 | 20.9 | 25.6 | 45.8 | 15.8 | 8.55 |
| 152 | BaMoO$_4$ (2) | 500 | 67.9 | 49.4 | 64.9 | 24.0 | 5.34 |

TABLE 11

| Ex. | Catalyst (g) | Temp (°C.) | Conv (%) Methanol | Selec (%) E | C | D | F |
|---|---|---|---|---|---|---|---|
| 153 | Li$_2$CO$_3$ (1) | 500 | 31.9 | 1.2 | 66.7 | — | — |
| 154 | Rb$_2$CO$_3$ (1) | 500 | 41.9 | 16.0 | 76.9 | 5.7 | — |
| 155 | Cs$_2$CO$_3$ (1) | 500 | 45.6 | 18.9 | 80.5 | 6.3 | — |
| 156 | BaWO$_4$ (1) | 500 | 25.3 | 9.1 | 69.3 | — | — |
| 157 | NaVO$_3$ (1) | 500 | 65.3 | 44.4 | 11.7 | — | — |

TABLE 12

| Ex. | Catalyst (g) | (*) | Molar ratio | Temp (°C.) | W/F | Conv (%) Methanol | Dimer | Selec (%) B | C | D | F |
|---|---|---|---|---|---|---|---|---|---|---|---|
| 158 | Alumina beads(100)—Ca(OH)$_2$(25)—NaOH(25) | 3 | 0.1/2.0 | 450 | 289 | 88.6 | 99.5(J) | 10.0 | 20.4 | 14.2 | 2.63 |
| 159 | Alumina beads(100)—Ca(OH)$_2$(25)—NaOH(25) | 3 | 0.05/1.0 | 450 | 211 | 99.2 | 99.8(K) | — | 23.8 | 23.4 | 5.37 |

J: cyclopentadiene dimer
K: methylcyclopentadiene dimer

We claim:

1. A method of alkylation of a cyclopentadiene derivative comprising the vapor-phase reaction of a cyclopentadiene derivative and an aliphatic lower alcohol in the presence of the following heterogeneous basic catalyst (A) or (B):
   (A) at least one member selected from the group consisting of oxides, hydroxides and salts of alkaline earth metals or alkali metals, provided that the oxide or hydroxide of an alkali metal is not solely used and that a combination of these two compounds is not used,
   (B) a mixture of the following (a) and (b):
      (a) at least one member selected from the group consisting of oxides, hydroxides and salts of alkaline earth metals or alkali metals,
      (b) at least one member selected from the group consisting of elements of groups (I) to (VIII), 2 to 7 periods of the periodic table, and oxides, hydroxides and carbonates of these elements, provided that oxides, hydroxides and carbonates of alkaline earth metals and alkali metals are excluded.

2. An alkylation method as defined in claim 1 wherein the cyclopentadiene derivative comprises cyclopentadiene, cyclopentadiene dimer, monomethylcyclopentadiene, monomethylcyclopentadiene dimer or alkylated derivatives thereof.

3. An alkylation method as defined in claim 1 wherein the aliphatic lower alcohol has 1 to 4 carbon atoms.

4. An alkylation method as defined in claim 1 wherein the salt of alkaline earth metal or alkali metal comprises a carbonate, phosphate, aluminate, tungstate, molybdate, stannate or metavanadate of these metals.

5. An alkylation method as defined in claim 1 wherein the oxide is one obtained by treating at a high temperature an element, hydroxide, carbonate, basic carbonate or organic acid salt of the metals, and ammonium salt of an oxygen-containing acid of the metals, or a metal salt or organometallic compound including the metal.

6. An alkylation method as defined in claim 1 wherein the oxide is one produced by calcination of the precipitated hydroxide or hydrated amorphous metal oxide obtained by hydrolysing or neutralizing with an aqueous ammonia solution a metal salt or metal halide.

7. An alkylation method as defined in claim 1 wherein the reaction is conducted at a temperature of 200° to 700° C.

8. An alkylation method as defined in claim 7 wherein the reaction is conducted at a temperature of 400° to 550° C.

* * * * *